(12) United States Patent
Breitscheidel et al.

(10) Patent No.: US 7,300,966 B2
(45) Date of Patent: Nov. 27, 2007

(54) METHOD FOR PRODUCING BLENDS OF PHTHALIC ACID DIESTERS, DECANOLS AND TRIDECANOLS

(75) Inventors: Boris Breitscheidel, Limburgerhof (DE); Richard Selberdinger, Hochdorf-Assenheim (DE); Klaus Rossato, Schifferstadt (DE); Uwe Storzum, Worms (DE); Jürgen Holzmann, Ludwigshafen (DE); Günther Golfier, Frankenthal (DE); Walter Disteldorf, Wachenheim (DE); Bernd Morsbach, Ludwigshafen (DE); Jarren Peters, Mannheim (DE); Christoph Übler, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 676 days.

(21) Appl. No.: 10/332,036

(22) PCT Filed: Jul. 4, 2001

(86) PCT No.: PCT/EP01/07637

§ 371 (c)(1),
(2), (4) Date: Jan. 6, 2003

(87) PCT Pub. No.: WO02/02499

PCT Pub. Date: Jan. 10, 2002

(65) Prior Publication Data

US 2003/0187114 A1 Oct. 2, 2003

(30) Foreign Application Priority Data

Jul. 5, 2000 (DE) .............................. 100 32 580
Jun. 12, 2001 (DE) .............................. 101 28 306

(51) Int. Cl.
*C08K 5/134* (2006.01)
*C09F 7/00* (2006.01)
*C07C 69/76* (2006.01)

(52) U.S. Cl. ...................... 524/296; 554/30; 560/76

(58) Field of Classification Search ................ 524/296; 560/76; 554/30
See application file for complete search history.

(56) References Cited

U.S. PATENT DOCUMENTS

| 4,216,337 | A | * | 8/1980 | Baba et al. ................... 560/78 |
| 5,661,204 | A | | 8/1997 | Bahrmann et al. .......... 524/296 |
| 5,849,972 | A | | 12/1998 | Vacari et al. ................ 548/222 |
| 5,880,310 | A | | 3/1999 | Ageishi et al. ............... 560/99 |
| 5,998,685 | A | * | 12/1999 | Nierlich et al. ............. 585/329 |
| 2004/0254393 | A1 | | 12/2004 | Godwin et al. ............... 560/98 |

FOREIGN PATENT DOCUMENTS

| DE | 43 39 713 | 5/1995 |
| EP | 4224 767 | 5/1991 |
| JP | A 6 345 928 | 12/1994 |
| WO | 01/36356 | 3/2001 |

OTHER PUBLICATIONS

JP-A 07 170 699 -Abst, scope of patent claims.
JP-A 08 283 510 -Abst, scope of patent claims.
JP-A 08 301 295 -Abst, scope of patent claims.
JA 81/47443—Abstract.
Catalysis Today, O'Connor et al, 1990, p. 329 ff.
JP-A 08 034 891 -Abst, scope of patent claims.
KA=83358-5-Abstract.
E.G. Maksimenko et al. in Plast. Massy 7, 42 (1980) as translated in Int. Polymer Sci. Technol. 8, T/8 (1981).
W. Dimler et al. XVI Ann. Techn. Conf. Soc. Plast. Engineers, Inc., Techn. Papers vol. VI, 57-1 (1960).

* cited by examiner

*Primary Examiner*—Taylor Victor Oh
(74) *Attorney, Agent, or Firm*—Novak Druce & Quigg, LLP

(57) ABSTRACT

A process is described for preparing mixtures of diesters of phthalic acid with decanols and tridecanols by reacting phthalic acid or a reactive derivative of phthalic acid with a mixture made from at least one decanol and at least one tridecanol.

Mixtures obtainable in this way are also described, as is their use as plasticizers for molding compositions, and also mixtures of isomeric tridecanols suitable for preparing the mixtures of diesters.

11 Claims, No Drawings

METHOD FOR PRODUCING BLENDS OF PHTHALIC ACID DIESTERS, DECANOLS AND TRIDECANOLS

The present invention relates to a process for preparing mixtures of diesters of phthalic acid with decanols and tridecanols.

The present invention further relates to mixtures of this type and to their use as plasticizers for molding compositions, and also to mixtures of isomeric tridecanols suitable for preparing the mixtures of diesters.

Long-chain alcohols, e.g. $C_{10}$, $C_{11}$, or $C_{13}$ alcohols, are widely used for preparing plasticizers. To this end, the alcohols are reacted with polycarboxylic acids, such as in particular phthalic acid, to give the corresponding esters.

Important members of this phthalate class of plasticizers are diisodecyl phthalates and diisotridecyl phthalates. They are mainly used in producing cable sheathing, and lines or pipes made from polyvinyl chloride (PVC), for example in automotive construction.

The prior art includes phthalate plasticizers whose alcohol units are $C_{10}$ alcohols (decanols) or $C_{13}$ alcohols (tridecanols):

JP-A 07 179 699 and JP-A 08 283 510 describe PVC-film plasticizers which are diesters of phthalic acid with a mixture composed of the $C_{10}$ alcohols 2-propylheptanol and 4-methyl-2-propylhexanol in a ratio by weight of from 88:12 to 70:30. JP-A 08 301 295 describes the use of esters of this type as plasticizers for PVC, in which the ratio by weight of 2-propylheptanol and 4-methyl-2-propylhexanol is from 100:0 to 50:50. JP-A 08 034 891 also discloses a PVC-film plasticizer based on 2-propylheptanol and 4-methyl-2-propylhexanol, and, in addition, a plasticizer of this type which contains 2-propylheptanol as sole alcohol unit.

JB 73/35705 and JA 81/47443 disclose the use of the diester of phthalic acid with tridecanol as a plasticizer for vinyl chloride polymers, such as PVC.

The skilled worker in the sector of PVC plastics, especially one concerned with the production of films, cables or lines made from this material, is increasingly frequently faced with the task of using plasticizers which on the one hand improve the plastic properties of these materials, primarily their low-temperature flexibility, but which on the other hand have only low volatility. Relatively low volatility is significant in helping to ensure that the flexibility achieved when the PVC plastic is prepared is retained in the long term, and that there is practically no emission of the plasticizer into the environment.

Known phthalate plasticizers with decanols or tridecanols as alcohol unit remain unsatisfactory in this regard.

It is an object of the present invention, therefore, to provide plasticizers which are based on esters of phthalic anhydride with alcohols having 10 or more carbon atoms and which can overcome the disadvantage described.

We have found that this object is achieved by means of a process for preparing mixtures of diesters of phthalic acid with decanols and tridecanols, which comprises reacting phthalic acid or a reactive derivative of phthalic acid with a mixture composed of at least one decanol and at least one tridecanol.

Mixtures of this type have also been found, as has their use as a plasticizer for molding compositions, and also mixtures of isomeric tridecanols suitable for preparing the mixtures of diesters.

The plasticizers of the invention bring about high low-temperature flexibility and have low volatility, superior to those of phthalic esters made from decanols alone or from tridecanols alone.

Preferred decanols are aliphatic monoalcohols having 10 carbon atoms, in particular the primary alkanols, the alkyl groups of which may be straight-chain or branched, for example n-decanol, methylnonanols, such as 1-methylnonanol, ethyl octanols, such as 1-ethyloctanol, propylheptanols, such as 1-propylheptanol, or methylpropylhexanols, in each case individually or in a mixture, and especially 2-propylheptanol on its own or 4-methyl-2-propylhexanol on its own. Particular preference is given to mixtures of the alcohols mentioned ("isodecanols"), particularly those with the CAS numbers 25339-17-7 and 93821-11-5. Very particular preference is given to mixtures in which 2-propylheptanol and 4-methyl-2-propylhexanol are present jointly and predominantly, preferably making up 80% by weight, especially 90% by weight, and in particular 95% by weight, and specifically in a ratio of from 99:1 to 1:99% by weight, preferably from 95:5 to 50:50% by weight, and particularly preferably from 92:8 to 88:12% by weight.

Preferred tridecanols are aliphatic monoalcohols having 13 carbon atoms, in particular the primary alkanols, the alkyl groups of which may be straight-chain or branched, for example n-tridecanol, methyldecanols [sic], such as 1-methyldodecanol, or ethylundecanols, such as 1-ethylundecanol, in each case either individually or in a mixture. Preference is given to mixtures of the alkanols mentioned ("isotridecanols"), and in particular those with the CAS numbers 27458-92-0 and 68526-86-3. Particular preference is given to isotridecanols obtainable by the following process:

In a multistage process starting from a hydrocarbon mixture comprising butenes, a first step dimerizes the butenes to give a mixture of isomeric octenes and dodecenes. The main product produced here is the octenes, while the proportion of dodecenes produced is generally from 5 to 20% by weight, based on the reactor discharge. The dodecenes are then isolated from the reaction mixture, hydroformylated to give the corresponding $C_{13}$ aldehydes, and then hydrogenated to give isotridecanols. The preparation of isotridecanols by this sequence of synthetis steps is known per se. However, the isotridecanols particularly preferred according to the invention are to be obtained only if specific defined parameters are complied with at least during the butene dimerization, and preferably during the butene dimerization and the hydroformylation.

It is therefore preferable to obtain the mixture of isomeric dodecenes by bringing a hydrocarbon mixture comprising butenes into contact with a heterogeneous catalyst which comprises nickel oxide. The isobutene content of the hydrocarbon mixture is preferably 5% by weight or less, in particular 3% by weight or less, particularly preferably 2% by weight or below, and most preferably 1.5% by weight or less, based in each case on the total butene content. A suitable hydrocarbon stream is what is known as the $C_4$ cut, a mixture composed of butenes and butanes, which is available in large amounts from FCC plants or steam crackers. Particular preference is given to the use of raffinate II as starting material, this being an isobutene-impoverished $C_4$ cut.

One preferred starting material comprises from 50 to 100% by weight, preferably from 80 to 95% by weight, of butenes, and from 0 to 50% by weight, preferably from 5 to 20% by weight, of butanes. The following composition of the butene fraction may be given as a general quantitative guideline:

| | |
|---|---|
| 1-butene | from 1 to 99% by weight |
| cis-2-butene | from 1 to 50% by weight |
| trans-2-butene | from 1 to 99% by weight |
| isobutene | from 1 to 5% by weight. |

Catalysts which may be used are catalysts known per se which comprise nickel oxide, e.g. as described by O'Connor et al. in Catalysis Today 6, (1990) p. 329. Supported nickel oxide catalysts may be used, suitable support materials being silica, alumina, aluminosilicates, aluminosilicates with a phyllosilicate structure, and zeolites. Particularly suitable catalysts are precipitation catalysts obtained by mixing aqueous solutions of nickel salts and silicates, e.g. mixing sodium silicate and nickel nitrate, where appropriate with other constituents, such as aluminum salts, e.g. aluminum nitrate, and calcining.

Particular preference is given to catalysts substantially composed of NiO, $SiO_2$, $TiO_2$ and/or $ZrO_2$, and also, where appropriate, $Al_2O_3$. Most preference is given to a catalyst whose active substantial constituents are from 10 to 70% by weight of nickel oxide, from 5 to 30% by weight of titanium dioxide and/or zirconium dioxide, and from 0 to 20% by weight of aluminum oxide, the remainder, to give 100% by weight, being silicon dioxide. A catalyst of this type is obtainable by precipitating the catalyst composition at a pH of from 5 to 9 by adding an aqueous solution comprising nickel nitrate to an alkali metal water glass solution which comprises titanium dioxide and/or zirconium dioxide, filtering, drying and annealing at from 350 to 650° C. Reference is made to DE-A 43 39 713 for details of the preparation of these catalysts. Reference is made to the entire disclosure of that publication.

The hydrocarbon mixture comprising butenes is preferably brought into contact with the catalyst at from 30 to 280° C., in particular from 30 to 140° C., and particularly preferably from 40 to 130° C. The pressure here is preferably from 10 to 300 bar, in particular from 15 to 100 bar, and particularly preferably from 20 to 80 bar. This pressure is usefully adjusted so that the olefin-rich hydrocarbon mixture is liquid or in the supercritical state at the temperature selected.

Examples of suitable apparatuses for bringing the hydrocarbon mixture comprising butenes into contact with the heterogeneous catalyst are tube-bundle reactors and shaft furnaces. Shaft furnaces are preferred because the capital expenditure costs are lower. The dimerization may be carried out in a single reactor, where the oligomerization catalyst may have been arranged in one or more fixed beds. Another way is to use a reactor cascade composed of two or more, preferably two, reactors arranged in series, where the butene dimerization in the reaction mixture is driven to only partial conversion on passing through the reactor or reactors preceding the last reactor of the cascade, and the desired final conversion is not achieved until the reaction mixture passes through the last reactor of the cascade. The butene dimerization preferably takes place in an adiabatic reactor or in an adiabatic reactor cascade.

After leaving the reactor or, respectively, the last reactor of a cascade, the dodecenes formed are separated off from the octenes and, where appropriate, from the higher oligomers, and from the unconverted butenes and butanes, in the reactor discharge. The octenes are generally the main product.

In the second step of the process, the dodecenes obtained are converted in a manner known per se into the aldehydes with molecules lengthened by one carbon atom, by hydroformylation using synthesis gas. The hydroformylation of olefins to prepare aldehydes is known per se and is described in J. Falbe (Ed.): "New Synthesis with Carbon monoxide", Springer Verlag, Berlin, 1980, for example. The hydroformylation takes place in the presence of catalysts dissolved homogeneously in the reaction medium. The catalysts used here are generally compounds or complexes of metals of the transition group VIII, especially compounds or, respectively, complexes of Co, Rh, Ir, Pd, Pt or Ru, these being either unmodified or modified with, for example, amine- or phosphine-containing compounds.

For the purposes of the present invention, the hydroformylation preferably takes place in the presence of a cobalt catalyst, preferably at from 120 to 240° C., in particular from 160 to 200° C., under a synthesis-gas pressure of from 150 to 400 bar, in particular from 250 to 350 bar. The hydroformylation preferably takes place in the presence of water. The mixing ratio of hydrogen to carbon monoxide in the synthesis gas used is preferably in the range from 70:30 to 50:50% by volume and in particular from 65:35 to 55:45% by volume.

The cobalt-catalyzed hydroformylation process may be carried out as a multistage process which comprises the following 4 stages: preparation of the catalyst (precarbonylation), catalyst extraction, olefin hydroformylation, and catalyst removal from the reaction product (decobaltization). In the first stage of the process, the precarbonylization, the starting material used is an aqueous cobalt salt solution, e.g. cobalt formate or cobalt acetate, which is reacted with carbon monoxide and hydrogen to prepare the catalyst complex ($HCo(CO)_4$) needed for the hydroformylation. In the second stage of the process, the catalyst extraction, the cobalt catalyst prepared in the first stage of the process is extracted from the aqueous phase using an organic phase, preferably using the olefin to be hydroformylated. Besides the olefin, it is sometimes useful to use the reaction products and byproducts from the hydroformylation for catalyst extraction, as long as these are insoluble in water and liquid under the selected reaction conditions. After separation of the phases, the organic phase loaded with the cobalt catalyst is fed to the third stage of the process, the hydroformylation. In the fourth stage of the process, the decobaltization, the organic phase of the reactor discharge is freed from the cobalt carbonyl complexes in the presence of complex-free process water by treatment with oxygen or air. During this, the cobalt catalyst is oxidatively broken down and the resultant cobalt salts are extracted back into the aqueous phase. The aqueous cobalt salt solution obtained from the decobaltization is recirculated into the first stage of the process, the precarbonylation. The crude hydroformylation product obtained may be fed directly to the hydrogenation. As an alternative, a $C_{13}$ aldehyde fraction may be isolated from this in a usual manner, e.g. by distillation, and fed to the hydrogenation.

The formation of the cobalt catalyst, the extraction of the cobalt catalyst into the organic phase, and the hydroformylation of the olefins may also be carried out in a single-stage process in the hydroformylation reactor.

Examples of cobalt compounds which may be used are cobalt(II) chloride, cobalt(II) nitrate, the amine or hydrate complexes of these, cobalt carboxylates, such as cobalt formate, cobalt acetate, cobalt ethylhexanoate, or cobalt naphthenoate, and also the cobalt caprolactamate complex. Under the hydroformylation conditions, the catalytically active cobalt compounds form in situ as cobalt carbonyls. It is also possible to use the carbonyl complexes of cobalt, such as dicobalt octacarbonyl, tetracobalt dodecacarbonyl, or hexacobalt hexadecacarbonyl.

The aldehyde mixture obtained during the hydroformylation is reduced to give primary alcohols. Some degree of reduction generally takes place under the hydroformylation conditions, and the hydroformylation here may also be controlled so that substantially complete reduction takes place. However, the hydroformylation product obtained is generally hydrogenated in another step of the process using hydrogen gas or a gas mixture comprising hydrogen. The hydrogenation generally takes place in the presence of a heterogeneous hydrogenation catalyst. The hydrogenation catalyst used may be any desired catalyst suitable for hydrogenating aldehydes to give primary alcohols. Examples of suitable catalysts available commercially are copper chromite, cobalt, cobalt compounds, nickel, nickel compounds, which may, where appropriate, comprise small amounts of chromium or other promoters, and mixtures of copper, nickel, and/or chromium. The nickel compounds are generally in supported form on support materials such as alumina or kieselguhr. It is also possible to use catalysts comprising precious metals, such as platinum or palladium.

The hydrogenation may take place by the trickle-flow method, where the mixture to be hydrogenated and the hydrogen gas or, respectively, the hydrogen-containing gas mixture are passed, for example concurrently, over a fixed bed of the hydrogenation catalyst.

The hydrogenation preferably takes place at from 50 to 250° C., in particular from 100 to 150° C., and at a hydrogen pressure of from 50 to 350 bar, in particular from 150 to 300 bar. Fractional distillation can be used to separate the desired isotridecanol fraction from the $C_8$ hydrocarbons and higher-boiling products present in the reaction discharge obtained during the hydrogenation.

The resultant isotridecanols particularly preferred for the purposes of the present invention have a characteristic distribution of isomers, which can be defined in more detail by means of gas chromatography, for example. The gas chromatogram can be divided into three retention regions, for example as described by Kovacs (Z. Anal. Chem. 181, (1961), p. 351; Adv. Chromatogr. 1 (1965), p. 229) with the aid of retention indices and using n-undecanol, n-dodecanol, and n-tridecanol as reference substances:

| Region 1: | Retention index <1180 |
| --- | --- |
| Region 2: | Retention index from 1180 to 1217 |
| Region 3: | Retention index >1217 |

The substances present in region 1 are mainly triply and more-than-triply branched isotridecanols, those present in region 2 are mainly doubly branched isotridecanols, and those present in region 3 are mainly singly-branched isotridecanols and n-tridecanol. For the purposes of the present invention, this method gives an adequately precise determination of the composition of isotridecanols by comparing the areas under the corresponding sections of the gas chromatogram curves (% by area).

Using the Kovacs method described, the particularly preferred isotridecanols of the invention generally have from 20 to 60% by area, preferably from 25 to 50% by area, particularly preferably from 40 to 48% by area, and very particularly preferably from 45 to 47% by area, of triply and more-than-triply branched isomers.

Using the Kovacs method described, the particularly preferred isotridecanols of the invention generally have from 10 to 50% by area, preferably from 20 to 45% by area, particularly preferably from 30 to 40% by area, and very particularly preferably from 35 to 38% by area, of doubly branched isomers.

Using the Kovacs method described, the particularly preferred isotridecanols of the invention generally have from 5 to 30% by area, preferably from 10 to 25% by area, particularly preferably from 15 to 20% by area, and very particularly preferably from 17 to 19% by area, of singly branched isomers and n-tridecanol.

The density of the particularly preferred isotridecanols is generally from 0.8 to 0.9 g/cm$^3$, preferably from 0.82 to 0.86 g/cm$^3$, and particularly preferably from 0.84 to 0.845 g/cm$^3$. Their refractive index $n_D^{20}$ is generally from 1.4 to 1.5, preferably from 1.44 to 1.46, and particularly preferably from 1.446 to 1.45. Their viscosity is generally from 30 to 40 mPas, preferably from 32 to 38 mPas, and particularly preferably from 34 to 35.5 mPas. Their boiling range is generally from 240 to 280° C., preferably from 250 to 275° C., and particularly preferably from 260 to 270° C.

The inventive diesters of phthalic acid are prepared in a manner known per se, by esterifying phthalic acid or a reactive phthalic acid derivative, such as phthalic anhydride or phthalic dichloride, using a mixture composed of at least one decanol and at least one tridecanol. It is preferable for the phthalic acid or the reactive phthalic acid derivative to be reacted with a molar excess of the alcohols, in particular a molar excess of from 5 to 30%, preferably in the presence of a Lewis acid as esterification catalyst, for example a dialkyl titanate, e.g. isopropyl butyl titanate, or of a Brönsted acid, such as methanesulfonic acid or sulfuric acid.

The reaction of the phthalic acid or of the reactive derivative of phthalic acid with the mixture made from at least one decanol and from at least one tridecanol generally takes place at from 150 to 300° C., preferably from 200 to 250° C.

It is preferable to use a molar excess of from 20 to 30%, preferably about 25%, of the mixture made from at least one decanol and from at least one tridecanol, based on phthalic acid or on the reactive derivative of phthalic acid.

An inert gas, such as nitrogen, may be passed through the reaction mixture during the reaction for continuous removal of water produced during the esterification process.

Once the reaction has ended, the reaction mixture is worked up to give the inventive mixture of esters of phthalic acid. The procedure here generally begins with very substantial removal particularly of organic contaminants and, where appropriate, unreacted decanol and/or tridecanol. This is preferably achieved by distilling off the excess alcohol in vacuo. The distillation is generally carried out at from 150 to 220° C., preferably from 180 to 200° C., at a pressure which is generally from 10 to 100 mbar, preferably from 40 to 60 mbar.

The crude ester mixture is then generally treated and thoroughly mixed with an aqueous alkali metal hydroxide solution, e.g. 1 percent strength by weight sodium hydroxide solution, the result being that the half ester and the catalyst are neutralized (and, where appropriate, hydrolyzed). It is normal for an aqueous phase and an organic phase to be formed here, the aqueuos phase being removed. A water wash of the organic phase may follow.

For further purification, the acid-free and washed ester mixture is preferably freed from organic contaminants and residual alcohols by stripping, using inert gas or steam. In a typical embodiment of this stripping procedure, the crude product is fed to the head, or to the vicinity of the head, of the stripping column, and nitrogen or steam is conducted in countercurrent through the column. The stripping procedure is generally carried out with a starting temperature for the crude product of from 130 to 220° C., preferably from 170 to 190° C., and at a pressure of from 10 to 100 mbar, preferably from 20 to 40 mbar. If the stripping time exceeds 2 hours in batchwise conduct of the process in the presence of water within the reaction mixture, the acid value of the product generally rises undesirably. The acid produced then has to be reneutralized, and the water removed from the neutralization process.

The purified ester mixture may then be dried at an elevated temperature in vacuo by passing a stream of nitrogen through the material, and, where appropriate, further purified by contact with an adsorbent, such as activated carbon or bleaching earth.

The molar ratio of decanols and tridecanols in the alcohol mixture used according to the invention is generally from 95:5 to 5:95, preferably from 85:15 to 15:85, particularly preferably from 75:25 to 25:75, and very particularly preferably from 75:25 to 65:35.

On the basis of a general knowledge of chemistry it may be assumed that the alcohols used according to the invention for preparing the ester mixtures do not all have the same reactivity towards the phthalic acid or the reactive derivative of phthalic acid, particularly since the alcohols have different electronic and stearic features. However, for practical purposes the composition of the ester mixture generally reflects sufficiently the composition of the alcohol mixture used for preparing the ester mixture.

The ester mixtures of the invention prepared in this way preferably comprise diesters of phthalic acid having in each case one decanol unit and one tridecanol unit, and also diesters having two decanol units or having two tridecanol units. If use is made of an alcohol mixture which is composed of from 60 to 70% by weight of decanols and from 30 to 40% by weight of tridecanols, the products obtained generally have the following composition: from 38 to 45% by weight of diesters with two $C_{10}$ alcohols, from 40 to 48% by weight of diesters with one $C_{10}$ and one $C_{13}$ alcohol, and from 12 to 15% by weight of diesters with two $C_{13}$ alcohols.

The process of the invention and the purification operations described can generally prepare ester mixtures with ester contents of more than 99.5% by weight.

If use is made of mixtures made from isomeric decanols and from isomeric tridecanols, a wide variety of ester mixtures is accessible. All of these ester mixtures are encompassed by the present invention. They are composed of phthalic esters which therefore can differ both with regard to the number of carbon atoms in the alcohol units of the ester groups and with regard to the branching of the alkyl chains within these alcohol units.

By using mixtures composed of isomeric decanols and isomeric tridecanols it is possible to obtain a wide variety of ester mixtures. All of these ester mixtures are included in the present invention. These mixtures are made of phthalic esters which may differ either with regard to the number of carbon atoms in the alcohol units within the ester groups or else with regard to the branching of the alkyl chains within these alcohol units.

The diester mixtures of the invention generally have a density of from 0.94 to 0.97 g/cm³ preferably from 0.945 to 0.965 g/cm³, and in particular from 0.95 to 0.96 g/cm³, a viscosity of from 100 to 200 mPas, preferably from 120 to 180 mPas, and in particular from 130 to 160 mPas, and a refractive index $n_D^{20}$ of from 1.475 to 1.495, preferably from 1.48 to 1.49, and in particular from 1.482 to 1.484.

The diester mixtures of the invention are suitable as plasticizers for molding compositions, in particular for PVC-based molding compositions. They are particularly suitable for preparing plasticized PVC compounds intended to have low plasticizer volatility together with very good cold-flexibility properties. The following method is preferably employed for preparing and testing the plasticized PVC compounds prepared using the diesters of the invention:

A mixture is prepared composed of PVC powder, preferably of a PVC powder prepared by the suspension process, and of an inventive diester of phthalic acid as plasticizer. Other additives may be added if desired, for example stabilizers, lubricants, fillers, pigments, dyes, flame retardants, light stabilizers, antistats, blowing agents, and biostabilizers. This mixture is then plasticized on a roll mill and roll-milled to give what is known as a milled sheet. The milled sheet is then pressed to give a plasticized PVC film, on which the performance tests are then carried out.

The cold-flexibility properties of plasticized PVC compounds are preferably characterized using what are known as the cold-crack temperature and the torsional rigidity.

The cold-crack temperature is the temperature at which a plasticized PVC compound begins to show visible damage under mechanical load at low temperatures. The cold-crack temperature was determined here to DIN 53372.

The torsional rigidity is the temperature at which a plasticized PVC compound can be twisted through a certain angle when a particular defined force is applied, and was determined here to DIN 53447.

Examples will now be used below to illustrate the invention in further detail:

EXAMPLES

Example 1

Preparation of a Mixture of Isomeric Tridecanols

Process Step 1 (Butene Dimerization)

The butene dimerization was carried out continuously in an adiabatic reactor composed of two subsidiary reactors (length: each 4 m, diameter: each 80 cm) with intermediate cooling at 30 bar. The starting material used was a raffinate II with the following composition:

| | |
|---|---|
| i-butane | 2% by weight |
| n-butane | 10% by weight |
| i-butene | 2% by weight |
| 1-butene | 32% by weight |
| trans-2-butene | 37% by weight |
| cis-2-butene | 17% by weight |

The catalyst used comprised a material as in DE-A 43 39 713, composed of 50% by weight of NiO, 12.5% by weight of $TiO_2$, 33.5% by weight of $SiO_2$ and 4% by weight of $Al_2O_3$, in the form of 5×5 mm tablets. The reaction was carried out with a throughput of 0.375 kg of raffinate II per liter of catalyst and hour, and with recycling of the reactor discharge freed from the oligomers formed, with a recycling ratio recycled material and raffinate II of 3, and with an entry temperature of 38° C. at the first subsidiary reactor, and with an entry temperature of 60° C. at the second subsidiary reactor. Conversion, based on the butenes present in the raffinate II, was 83.1%, octene selectivity was 83.3%, and dodecene selectivity was 12%. Fractional distillation of the reactor discharge was used to separate the dodecene fraction from unconverted raffinate II, the octenes and the high-boilers.

Process Step 2(Hydroformylation Followed by Hydrogenation)

750 g of the dodecene mixture prepared in step 1 of the process were reacted for 5 hours batchwise in an autoclave with 0.13% by weight of dicobalt octacarbonyl ($Co_2(CO)_8$) as catalyst, with addition of 75 g of water, at 185° C. and under a synthesis-gas pressure of 280 bar, with a mixing ratio $H_2$ and CO of 60:40% by volume. The consumption of synthesis gas, detectable by a pressure fall-off in the autoclave, was compensated by introducing more gas under pressure. Once the pressure in the autoclave had been reduced, the reactor discharge, with 10% strength by weight of acetic acid, was freed oxidatively from the cobalt catalyst by introducing air, and the organic product phase was hydrogenated using Raney nickel at 125° C. and with a hydrogen pressure of 280 bar for 10 h. Fractional distillation of the reactor discharge was used to separate the isotridecanol fraction from the $C_{12}$ paraffins and the high boilers.

Using the Kovacs method (see above) to determine percentage areas from gas chromatography, the proportion of triply and more-than triply branched isotridecanols in the resultant isotridecanol was 45.8%, that of doubly branched isotridecanols was 36.8%, and the proportion of singly branched isotridecanols together with n-tridecanol was determined at 17.4%. The procedure here was as follows:

A specimen of the isotridecanol was trimethylsilylated using 1 ml of N-methyl-N-trimethylsilyltrifluoroacetamide per 100 µl of specimen for 60 minutes at 80° C. For separation by gas chromatography use was made of a Hewlett Packard Ultra 1 separating column of 50 m in length, based on 100%-methylated silicone rubber, with an internal diameter of 0.32 mm, with a film thickness of 0.33 µm. Injector temperature and detector temperature were 250° C. and the oven temperature was 160° C. (isothermal). The split was 80 ml/min. The carrier gas was nitrogen. The inlet pressure was set to 2 bar. 1 µl of the specimen was injected into the gas chromatograph, and the separated constituents were detected by means of FID. For evaluation purposes the gas chromatogram was subdivided into the following regions:

| | |
|---|---|
| Region 1 | Retention index <1180 |
| Region 2 | Retention index from 1180 to 1217 |
| Region 3 | Retention index >1217. |

The reference substances used here were

| | |
|---|---|
| n-undecanol | Retention index 1100 |
| n-tridecanol [sic] | Retention index 1200 and |
| n-tridecanol | Retention index 1300. |

The areas of the tridecanol peaks were set to 100 percent by area.

The density of the isotridecanol was 0.843 g/cm³, the refractive index $n_D^{20}$ was 1.448, the viscosity was 34.8 mPas, and the boiling range was from 261 to 267° C.

Example 2

Preparation and testing of an inventive diester of the invention made from phthalic acid and from a mixture of decanols and tridecanols in a molar ratio of 70:30

307.81 g of the isotridecanol from Example 1 and 569.09 g of a mixture of 2-propylheptanol and 4-methyl-2-propylhexanol in a ratio by weight of 89:11 (20% alcohol excess, based on phthalic anhydride) were reacted with 316.98 g of phthalic anhydride and 0.41 g of isopropyl butyl titanate as catalyst, in a 2 l autoclave into which $N_2$ was bubbled (10 l/h) at 230° C. using a stirring rate of 500 rpm. The water of reaction formed was continuously removed with the $N_2$ stream from the reaction mixture. The reaction time was 180 min. The alcohol excess was then distilled off at a reduced pressure of 50 mbar. 1000 g of the crude phthalate were neutralized with 150 ml of 0.5% strength by weight sodium hydroxide solution by stirring at 80° C. for 10 minutes in order to remove acidic monomer components, e.g. incompletely esterified phthalic acid. A two-phase mixture formed, with an upper organic phase and a lower aqueous phase (washings with hydrolyzed catalyst). The aqueous phase was separated off, and the organic phase was washed again twice with 200 ml of water. For further purification, the neutralized and washed phthalate was treated with steam at 180° C. at a reduced pressure of 50 mbar for 2 h, low boilers thereby being removed. The purified phthalate was then dried for 30 min at 150° C./50 mbar by passing a stream of $N_2$ (2 l/h) through it, then mixed with activated carbon by stirring for 5 min and filtered off with suction at 80° C. through a filter funnel using the filtration aid "Supra"-Theorit 5.

The resultant mixture of diesters had a density of 0.957 g/cm³, a viscosity of 138 mPas, a refractive index $n_D^{20}$ of 1.483, an acid value of 0.027 mg KOH/g, a water content of 0.029% by weight, and a purity of 99.83% by GC.

150 g of "Vinoflex S 7114" suspension PVC (Solvin), 100 g of the phthalate of the invention, and 3 g of "Lankromark LZB 753" Ba/Zn stabilizer were mixed at room temperature using a manual mixer. The mixture was then plasticized on a steam-heated laboratory roll mill (Collin "150") and processed to give a milled sheet. The temperature of each of the two rolls was 170° C., and the rotation rates were 15 rpm (front roll) and 12 rpm (rear roll), and the milling time was 5 minutes. This gave a milled sheet with a thickness of 0.55 mm. The cooled milled sheet was then pressed at 180° C. at a pressure of 220 bar for 400 s in a Collin "400 P" press to give a plasticized PVC film with a thickness of 0.50 mm.

The volatility of the plasticizer was then determined by the following method on this plasticized PVC film:

A specimen holder for four vertically suspended film specimens was attached to the inner top surface of a commercially available Heraeus T 5042 E laboratory drying cabinet of interior dimensions 42 (width)×35 (height)×32 (depth) cm. The axis of this sample holder was driven by an electric motor at 2 rpm. The dimensions of the film specimens were 100×150×0.5 mm. They were weighed before the experiment and then suspended from the specimen holder using a perforation on the short side of each specimen. The upper edges of the films here were 70 mm distant from the top inner surface of the cabinet. Arranged on the floor of the cabinet there was an air-circulator box, covered with a "Sika B 100" sintered metal sheet and producing a laminar air flow within the cabinet. The air throughput was set to 800 l/h, corresponding to an air change rate of from 17 to 18 air changes per hour. The temperature of 130° C. was monitored by a temperature sensor whose tip had been positioned in the middle of the cabinet, 100 mm below the top inner surface. An exhaust tube led from the cabinet interior to a condensation apparatus for the plasticizer. The experiment lasted 24 hours, after which the four specimens of film were weighed and the average percentage weight loss calculated.

The cold-crack temperature was determined to DIN 53372, and the torsional rigidity to DIN 53447. The results are given in Table 1.

Example 3

Preparation and testing of a diester of the invention made from phthalic acid and from a mixture of decanols and tridecanols in a molar ratio of 50:50

505.01 g of the isotridecanol from Example 1 and 398.89 g of a mixture of 2-propylheptanol and 4-methyl-2-propylhexanol in a weight ratio of 89:11 were reacted, as in Example 2, with 311.05 g of phthalic anhydride and 0.41 g of isopropyl butyl titanate as catalyst.

The resultant mixture of diesters had a density of 0.953 g cm$^3$, a viscosity of 146.0 mPas, a refractive index $n_D^{20}$ of 1.483, an acid value of 0.027 mg KOH/g, a water content of 0.028% by weight, and a purity of 99.77% by GC.

Using methods similar to those of Example 2, a plasticized PVC compound was prepared using the phthalate of the invention, and tested. The results are given in Table 1.

Example 4

Preparation and testing of a diester of the invention made from phthalic acid and from a mixture of decanols and tridecanols in a molar ratio of 30:70

740.68 g of the isotridecanol from Example 1 and 250.73 g of a mixture of 2-propylheptanol and 4-methyl-2-propylhexanol in a weight ratio of 89:11 were reacted, as in Example 2, with 325.86 g of phthalic anhydride and 0.41 g of isopropyl butyl titanate as catalyst.

The resultant mixture of diesters had a density of 0.950 g cm$^3$, a viscosity of 157.0 mPas, a refractive index $n_D^{20}$ of 1.483, an acid value of 0.035 mg KOH/g, a water content of 0.027% by weight, and a purity of 99.81% by GC.

Using methods similar to those of Example 2, a plasticized PVC compound was prepared using the phthalate of the invention, and tested. The results are given in Table 1.

Examples 5-7

Comparative Examples

Using methods similar to those in Examples 2 to 4, plasticized PVC films were prepared using the commercially available plasticizers: BASF Palatinol Z (a diisodecyl phthalate), BASF Palatinol 10-P (a di-2-propylheptyl phthalate), and BASF Palatinol CE 5455 (a diisotridecyl phthalate). Using these films, the volatility of the plasticizer was determined by the method described above, the cold-crack temperature was determined to DIN 53372 and the torsional rigidity was determined to DIN 53447. The results are given in Table 1.

TABLE 1

Results of performance tests on plasticizers

| | Volatility (% weight loss from the specimen) | Cold-crack temperature to DIN 53372 [° C.] | Torsional rigidity to DIN 53447 [° C.] |
|---|---|---|---|
| Example 2, Inventive | 0.68 | −41 | −41 |
| Example 3, Inventive | 0.54 | −42 | −43 |
| Example 4, Inventive | 0.38 | −43 | −44 |
| Example 5, Comparison: BASF Palatinol Z | 0.9 | −36 | −35 |
| Example 6, Comparison: BASF Palatinol 10-P | 1.2 | −35 | −38 |
| Example 7, Comparison: BASF Palatinol CE 5455 | 0.5 | −30 | −37 |

Table 1 shows that the volatility of the plasticizers of the invention is comparable with, or can even be superior to, that of the best comparative product, namely BASF Palatinol CE 5455, a diisotridecyl phthalate. In addition, the plasticizers of the invention have markedly improved, i.e. lower, cold-crack temperatures and torsional rigidities when compared with all three of the comparative products (BASF Palatinols of grades Z, 10-P, and CE 5455).

We claim:

1. A mixture of diesters of phthalic acid, obtained by reacting phthalic acid or phthalic anhydride and phthalic acid dichloride with an alcohol mixture at from 150 to 300° C., wherein
    the alcohol mixture consists of one or more decanols and one or more tridecanols,
    the one or more decanols of the alcohol mixture are a decanol mixture consisting essentially of 2-propylheptanol and 4-methyl-2-propylhexanol, and
    the one or more tridecanols of the alcohol mixture are a mixture of isomeric tridecanols.

2. A mixture of diesters of phthalic acid with alcohols selected from the group consisting of decanols and tridecanols, wherein
    from 38 to 45% by weight of the diesters are diesters with two $C_{10}$ alcohols,
    from 40 to 48% by weight of the diesters are diesters with one $C_{10}$ alcohol and one $C_{13}$ alcohol, and
    from 10 to 15% by weight of the diesters are diesters with two $C_{13}$ alcohols.

3. A molding composition comprising a molding material and as a plasticizer the mixture of diesters of phthalic acid defined in claim 1.

4. The molding composition defined in claim 3 wherein the molding material is a PVC-based molding material.

5. A method of plasticizing a molding composition which comprises adding to the molding composition as a plasticizer the mixture of diesters of phthalic acid defined in claim 1.

6. The method of claim 5, wherein the molding composition is a PVC-based molding material.

7. A mixture of diesters of phthalic acid with decanols and tridecanols as defined in claim 2, wherein the mixture of isomeric tridecanols comprises
    from 20 to 60% of triply or more-than-triply branched tridecanols, from 10 to 50% of doubly branched tridecanols, and
from 5 to 30% of singly branched tridecanols and/or of tridecanol,
where the percentages give the areas determined by gas chromatography relative to the total area over all the tridecanols present in the mixture analyzed, and which mixture is obtained by a process comprising a hydroformylation and hydrogenation of a mixture of isomeric dodecenes.

8. A mixture of diesters of phthalic acid with decanols and tridecanols as defined in claim 7, which is obtained by a process which further comprises preparing the mixture of isomeric dodecenes by reacting a hydrocarbon mixture comprising butenes on a heterogeneous catalyst which comprises nickel oxide.

9. A mixture of diesters of phthalic acid with decanols and tridecanols as defined in claim 8, in which the heterogeneous catalyst comprises, as active constituents, from 10 to 70% by weight of nickel oxide, from 5 to 30% by weight of titanium dioxide and/or zirconium dioxide, and from 0 to 20% by weight of aluminum oxide, the remainder, to give 100% by weight, being silicon dioxide.

10. A mixture of diesters of phthalic acid with decanols and tridecanols as defined in claim 7, wherein the mixture of isomeric tridecanols has been obtained by a process in which the mixture of isomeric dodecenes is hydroformylated in the presence of a cobalt catalyst.

11. A mixture of diesters of phthalic acid with decanols and tridecanols as defined in claim 2, wherein the $C_{10}$-alcohols of the diesters consist essentially of 2-propylheptanol and 4-methyl-2-propylhexanol and the $C_{13}$-alcohols of the diesters are a mixture of isomeric tridecanols.

* * * * *